United States Patent [19]
Everhart et al.

[11] Patent Number: 5,389,202
[45] Date of Patent: Feb. 14, 1995

[54] PROCESS FOR MAKING A HIGH PULP CONTENT NONWOVEN COMPOSITE FABRIC

[75] Inventors: Cherie H. Everhart, Alpharetta, Ga.; Daniel O. Fischer, Knoxville, Tenn.; Fred R. Radwanski, Roswell, Ga.; Henry Skoog, Roswell, Ga.

[73] Assignee: Kimberly-Clark Corporation, Neenah, Wis.

[21] Appl. No.: 74,571

[22] Filed: Jun. 9, 1993

Related U.S. Application Data

[62] Division of Ser. No. 633,594, Dec. 21, 1990, abandoned.

[51] Int. Cl.⁶ .............................................. D21H 23/24
[52] U.S. Cl. .................................... 162/103; 162/108; 162/109; 162/115; 162/125; 162/127; 162/128; 162/129; 162/130; 162/136; 162/146; 162/158; 162/168.1; 162/175; 162/181.1; 162/181.8; 162/181.9; 162/184; 162/201; 162/204; 28/104
[58] Field of Search .............. 162/115, 109, 103, 104, 162/125, 129, 130, 131, 132, 146, 108, 127, 128, 136, 168.1, 158, 175, 181.1, 181.8, 181.9, 184, 201, 204; 28/104

[56] References Cited

U.S. PATENT DOCUMENTS

| | | | |
|---|---|---|---|
| 2,862,251 | 12/1958 | Kalwaites | 19/161 |
| 3,284,857 | 11/1966 | Hynek | 19/161 |
| 3,330,009 | 7/1967 | Hynek | 19/161 |
| 3,336,182 | 8/1967 | Bassett et al. | 161/110 |
| 3,486,168 | 12/1969 | Evans et al. | 161/169 |
| 3,493,462 | 2/1970 | Bunting et al. | 161/169 |
| 3,494,821 | 2/1970 | Evans | 161/169 |
| 3,498,874 | 3/1970 | Evans et al. | 161/109 |
| 3,560,326 | 2/1971 | Bunting et al. | 161/169 |
| 3,620,903 | 11/1971 | Bunting et al. | 161/169 |
| 4,410,579 | 10/1983 | Johns | 428/131 |
| 4,442,161 | 4/1984 | Kirayoglu et al. | 428/219 |
| 4,542,060 | 9/1985 | Yoshida et al. | 428/287 |
| 4,582,666 | 4/1986 | Kenworthy et al. | 264/557 |
| 4,755,421 | 7/1988 | Manning et al. | 428/224 |
| 4,775,579 | 10/1988 | Hagy et al. | 428/284 |
| 4,808,467 | 2/1989 | Suskind et al. | 428/284 |
| 4,879,170 | 11/1989 | Radwanski et al. | 428/233 |
| 4,931,355 | 6/1990 | Radwanski et al. | 428/283 |
| 4,939,016 | 7/1990 | Radwanski et al. | 428/152 |
| 4,950,531 | 8/1990 | Radwanski et al. | 428/284 |
| 5,151,320 | 9/1992 | Homonoff et al. | 428/284 |

FOREIGN PATENT DOCUMENTS

| | | |
|---|---|---|
| 841938 | 5/1970 | Canada . |
| 128667 | 12/1984 | European Pat. Off. . |
| 159630A | 10/1985 | European Pat. Off. . |
| 223614A | 5/1987 | European Pat. Off. . |
| 304825A2 | 3/1989 | European Pat. Off. . |
| 308320A | 3/1989 | European Pat. Off. . |
| 333211A | 9/1989 | European Pat. Off. . |
| 373974A | 6/1990 | European Pat. Off. . |
| 472355A1 | 2/1992 | European Pat. Off. . |
| 90/04060 | 4/1990 | WIPO . |

OTHER PUBLICATIONS

*Spunlace Technology Today*, Miller Freeman Publications, Inc., San Francisco, Calif., Copyright © 1989, p. 129.

Primary Examiner—Peter Chin
Attorney, Agent, or Firm—Karl V. Sidor

[57] ABSTRACT

A high pulp content nonwoven composite fabric is disclosed. The composite fabric contains more than about 70 percent, by weight, pulp fibers which are hydraulically entangled into a continuous filament substrate. This high pulp content composite nonwoven fabric may be used as a heavy duty wiper or as a fluid distribution material, cover material, and/or absorbent material in an absorbent personal care product. Also disclosed is a method of making the high pulp content nonwoven composite fabric.

23 Claims, 7 Drawing Sheets

PROCESS FOR MAKING A HIGH PULP CONTENT NONWOVEN COMPOSITE FABRIC

This application is a divisional application of application Ser. No. 07/633,594 filed on Dec. 21, 1990, now abandoned.

FIELD OF THE INVENTION

The present invention relates to a hydraulically entangled nonwoven composite fabric containing pulp fibers and a method for making a nonwoven composite fabric.

BACKGROUND OF THE INVENTION

Although nonwoven webs of pulp fibers are known to be absorbent, nonwoven webs made entirely of pulp fibers may be undesirable for certain applications such as, for example, heavy duty wipers because they lack strength and abrasion resistance. In the past, pulp fiber webs have been externally reinforced by application of binders. For example, binders may be printed onto one or more sides of a wet laid web of pulp fibers to provide an absorbent wiper having strength and abrasion resistance. Typically, such externally reinforced wipers have contained up to about 25 percent, by weight, binder. Such high levels of binders can add expense and leave streaks during use which may render a surface unsuitable for certain applications such as, for example, automobile painting. Binders may also be leached out when such externally reinforced wipers are used with certain volatile or semi-volatile solvents.

Pulp fibers and/or pulp fiber webs have also been combined with materials such as, for example, nonwoven spunbonded webs, meltblown webs, scrim materials, and textile materials. One known technique for combining these materials is by hydraulic entangling. For example, U.S. Pat. No. 4,808,467 to Suskind discloses a high-strength nonwoven fabric made of a mixture of wood pulp and textile fibers entangled with a continuous filament base web.

Laminates of pulp fibers with textiles and/or nonwoven webs are disclosed in Canadian Patent No. 841,398 to Shambelan. According to that patent, high pressure jet streams of water may be used to entangle an untreated paper layer with base webs such as, for example, a continuous filament web.

European patent application 128,667 discloses an entangled composite fabric having an upper and lower surface. The upper surface is disclosed as having been formed of a printed re-pulpable paper sheet. The other surface is disclosed as having been formed from a base textile layer which may be, for example, a continuous filament nonwoven web. According to that patent application, the layers are joined by entangling the fibers of the pulp layer with those of the base layer utilizing columnar jets of water.

While these references are of interest to those practicing water-jet entanglement of fibrous materials, they do not address the need for a high pulp content nonwoven composite fabric which has strength and abrasion resistance and which may be used as a high strength wiper. There is still a need for an inexpensive high strength wiper which is able to quickly absorb several times its weight in water, aqueous liquid or oil. There is also a need for a high pulp content reinforced wiper which contains a substantial proportion of low-average fiber length pulp and which is able to quickly absorb several times its weight in water, aqueous liquid or oil. A need exists for a high pulp content composite fabric that can be used as a wiper or as a fluid distribution layer and/or absorbent component of an absorbent personal care product. There is also a need for a practical method of making a high pulp content nonwoven composite fabric. This need also extends to a method of making such a composite fabric which contains a substantial proportion of low-average fiber length pulp. Meeting this need is important since it is both economically and environmentally desirable to substitute low-average fiber length secondary (i.e., recycled) fiber pulp for high-quality virgin wood fiber pulp and still provide a high pulp content composite fabric that can be used as a wiper or as a fluid distribution layer and/or absorbent component of an absorbent personal care product.

DEFINITIONS

The term "machine direction" as used herein refers to the direction of travel of the forming surface onto which fibers are deposited during formation of a nonwoven web.

The term "cross-machine direction" as used herein refers to the direction which is perpendicular to the machine direction defined above.

The term "pulp" as used herein refers to fibers from natural sources such as woody and non-woody plants. Woody plants include, for example, deciduous and coniferous trees. Non-woody plants include, for example, cotton, flax, esparto grass, milkweed, straw, jute hemp, and bagasse.

The term "average fiber length" as used herein refers to a weighted average length of pulp fibers determined utilizing a Kajaani fiber analyzer model No. FS-100 available from Kajaani Oy Electronics, Kajaani, Finland. According to the test procedure, a pulp sample is treated with a macerating liquid to ensure that no fiber bundles or shives are present. Each pulp sample is disintegrated into hot water and diluted to an approximately 0.001% solution. Individual test samples are drawn in approximately 50 to 100 ml portions from the dilute solution when tested using the standard Kajaani fiber analysis test procedure. The weighted average fiber length may be expressed by the following equation:

$$\sum_{x_i=0}^{k} (x_i * n_i)/n$$

where k = maximum fiber length
$x_i$ = fiber length
$n_i$ = number of fibers having length $x_i$
n = total number of fibers measured.

The term "low-average fiber length pulp" as used herein refers to pulp that contains a significant amount of short fibers and non-fiber particles. Many secondary wood fiber pulps may be considered low average fiber length pulps; however, the quality of the secondary wood fiber pulp will depend on the quality of the recycled fibers and the type and amount of previous processing. Low-average fiber length pulps may have an average fiber length of less than about 1.2 mm as determined by an optical fiber analyzer such as, for example, a Kajaani fiber analyzer model No. FS-100 (Kajaani Oy Electronics, Kajaani, Finland). For example, low average fiber length pulps may have an average fiber length ranging from about 0.7 to 1.2 mm. Exemplary low average fiber length pulps include virgin hardwood pulp, and secondary fiber pulp from sources such as, for example, office waste, newsprint, and paperboard scrap.

The term "high-average fiber length pulp" as used herein refers to pulp that contains a relatively small amount of short fibers and non-fiber particles. High-average fiber length pulp is typically formed from certain non-secondary (i.e., virgin) fibers. Secondary fiber pulp which has been screened may also have a high-average fiber length. High-average fiber length pulps typically have an average fiber length of greater than about 1.5 mm as determined by an optical fiber analyzer such as, for example, a Kajaani fiber analyzer model No. FS-100 (Kajaani Oy Electronics, Kajaani, Finland). For example, a high-average fiber length pulp may have an average fiber length from about 1.5 mm to about 6 mm. Exemplary high-average fiber length pulps which are wood fiber pulps include, for example, bleached and unbleached virgin softwood fiber pulps.

As used herein, the term "spunbonded filaments" refers to small diameter continuous filaments which are formed by extruding a molten thermoplastic material as filaments from a plurality of fine, usually circular, capillaries of a spinnerette with the diameter of the extruded filaments then being rapidly reduced as by, for example, eductive drawing and/or other well-known spunbonding mechanisms. The production of spun-bonded nonwoven webs is illustrated in patents such as, for example, in U.S. Pat. No. 4,340,563 to Appel et al., and U.S. Pat. No. 3,692,618 to Dorschner et al. The disclosures of these patents are hereby incorporated by reference.

SUMMARY OF THE INVENTION

The present invention addresses the needs discussed above by providing a high pulp content nonwoven composite fabric. The composite fabric contains more than about 70 percent, by weight, pulp fibers which are hydraulically entangled into a nonwoven continuous filament substrate that makes up less than about 30 percent, by weight, of the fabric. For example, the nonwoven composite fabric may contain from about 10 to about 25 percent, by weight of the nonwoven continuous filament substrate and from about 75 to about 90 percent, by weight, pulp fibers.

The continuous filament nonwoven substrate may be a nonwoven web of continuous spunbonded filaments. In one aspect of the present invention, the nonwoven continuous filament substrate may have a total bond area of less than about 30 percent (as determined by optical microscopic methods) and a bond density greater than about 100 pin bonds per square inch. For example, the nonwoven continuous filament substrate may have a total bond area from about 2 to about 30 percent and a bond density of about 100 to about 500 pin bonds per square inch. As a further example, the nonwoven continuous filament substrate may have a total bond area from about 5 to about 20 percent and a bond density of about 250 to 350 pin bonds per square inch.

The pulp fiber component of the composite nonwoven fabric may be woody and/or non-woody plant fiber pulp. The pulp may be a mixture of different types and/or qualities of pulp fibers. For example, one embodiment of the invention includes a pulp containing more than about 50% by weight, low-average fiber length pulp and less than about 50% by weight, high-average fiber length pulp (e.g., virgin softwood pulp). The low-average fiber length pulp may be characterized as having an average fiber length of less than about 1.2 mm. For example, the low-average fiber length pulp may have a fiber length from about 0.7 mm to about 1.2 mm. The high-average fiber length pulp may be characterized as having an average fiber length of greater than about 1.5 mm. For example, the high-average fiber length pulp may have an average fiber length from about 1.5 mm to about 6 mm. One exemplary fiber mixture contains about 75 percent, by weight, low-average fiber length pulp and about 25 percent, by weight, high-average fiber length pulp.

According to the invention, the low-average fiber length pulp may be certain grades of virgin hardwood pulp and low-quality secondary (i.e., recycled) fiber pulp from sources such as, for example, newsprint, reclaimed paperboard, and office waste. The high-average fiber length pulp may be bleached and unbleached virgin softwood pulps.

The present invention also contemplates treating the nonwoven composite fabric with small amounts of materials such as, for example, binders, surfactants, cross-linking agents, de-bonding agents, fire retardants, hydrating agents and/or pigments. Alternatively and/or additionally, the present invention contemplates adding particulates such as, for example, activated charcoal, clays, starches, and superabsorbents to the nonwoven composite fabric.

The nonwoven composite fabric may be used as a heavy duty wiper or as a fluid distribution material in an absorbent personal care product. In one embodiment, the nonwoven composite material may be a single-ply or multiple-ply wiper having a basis weight from about 20 to about 200 grams per square meter (gsm). For example, the wiper may have a basis weight between about 25 to about 150 gsm or more particularly, from about 30 to about 110 gsm. The wiper desirably has a water capacity greater than about 450 percent, an oil capacity greater than about 250 percent, a water wicking rate (machine direction) greater than about 2.0 cm per 15 seconds, and oil wicking rate (machine direction) greater than about 0.5 cm per 15 seconds. When used as a fluid management material in a personal care product, the nonwoven composite fabric may have about the same properties as the wiper embodiment except for a basis weight which may range from about 40 to about 170 gsm, for example, from about 60 to about 120 gsm. Additionally, one or more layers of the nonwoven composite fabric may be used as an absorbent component of a personal care product, especially with added superabsorbent material. When used as an absorbent component, the nonwoven composite fabric may have a basis weight of 100 gsm or more and may also serve as a fluid distribution material. For example, the nonwoven composite material may have a basis weight from about 100 to about 350 gsm.

The present invention also contemplates a method of making a high pulp content nonwoven composite fabric by superposing a pulp fiber layer over a nonwoven continuous filament substrate having a total bond area of less than about 30 percent and a bond density of greater than about 100 pin bonds per square inch; hydraulically entangling the layers to form a composite material; and then drying the composite.

According to the invention, the layers may be superposed by depositing pulp fibers onto the nonwoven continuous filament substrate by dry forming or wet-forming processes. The layers may also be superposed by overlaying the nonwoven continuous filament substrate layer with a coherent pulp fiber sheet. The coherent pulp fiber sheet may be, for example, a re-pulpable paper sheet, a re-pulpable tissue sheet or a batt of wood pulp fibers.

The hydraulically entangled nonwoven composite fabric may be dried utilizing a non-compressive drying process. Through-air drying processes have been found to work particularly well. Other drying processes which incorporate infra-red radiation, yankee dryers, steam cans, vacuum de-watering, microwaves, and ultrasonic energy may also be used.

DETAILED DESCRIPTION OF THE INVENTION

Figure 1:
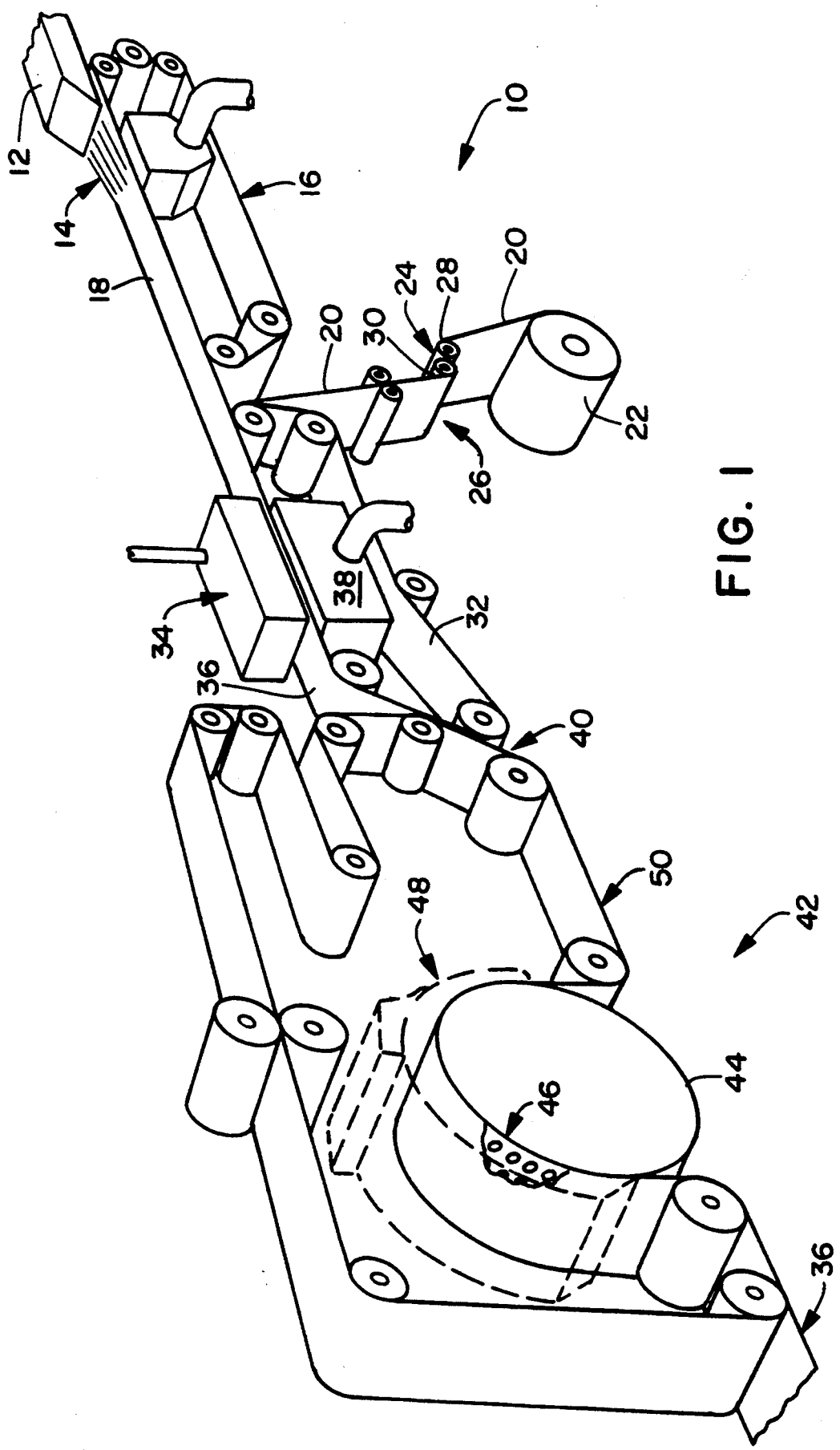
FIG. 1 is an illustration of an exemplary process for making a high pulp content nonwoven composite fabric.

Referring to FIG. 1 of the drawings there is schematically illustrated at 10 a process for forming a high pulp content nonwoven composite fabric. According to the present invention, a dilute suspension of pulp fibers is supplied by a head-box 12 and deposited via a sluice 14 in a uniform dispersion onto a forming fabric 16 of a conventional papermaking machine. The suspension of pulp fibers may be diluted to any consistency which is typically used in conventional papermaking processes. For example, the suspension may contain from about 0.01 to about 1.5 percent by weight pulp fibers suspended in water. Water is removed from the suspension of pulp fibers to form a uniform layer of pulp fibers 18.

The pulp fibers may be any high-average fiber length pulp, low-average fiber length pulp, or mixtures of the same. The high-average fiber length pulp typically have an average fiber length from about 1.5 mm to about 6 mm. Exemplary high-average fiber length wood pulps include those available from the Kimberly-Clark Corporation under the trade designations Longlac 19, Coosa River 56, and Coosa River 57.

The low-average fiber length pulp may be, for example, certain virgin hardwood pulps and secondary (i.e. recycled) fiber pulp from sources such as, for example, newsprint, reclaimed paperboard, and office waste. The low-average fiber length pulps typically have an average fiber length of less than about 1.2 mm, for example, from 0.7 mm to 1.2 mm.

Mixtures of high-average fiber length and low-average fiber length pulps may contain a significant proportion of low-average fiber length pulps. For example, mixtures may contain more than about 50 percent by weight low-average fiber length pulp and less than about 50 percent by weight high-average fiber length pulp. One exemplary mixture contains 75 percent by weight low-average fiber length pulp and about 25 percent high-average fiber length pulp.

The pulp fibers used in the present invention may be unrefined or may be beaten to various degrees of refinement. Small amounts of wet-strength resins and/or resin binders may be added to improve strength and abrasion resistance. Useful binders and wet-strength resins include, for example, Kymene 557 H available from the Hercules Chemical Company and Parez 631 available from American Cyanamid, Inc. Cross-linking agents and/or hydrating agents may also be added to the pulp mixture. Debonding agents may be added to the pulp mixture to reduce the degree of hydrogen bonding if a very open or loose nonwoven pulp fiber web is desired. One exemplary debonding agent is available from the Quaker Chemical Company, Conshohocken, Pa., under the trade designation Quaker 2008. The addition of certain debonding agents in the amount of, for example, 1 to 4 percent, by weight, of the composite also appears to reduce the measured static and dynamic coefficients of friction and improve the abrasion resistance of the continuous filament rich side of the composite fabric. The de-bonder is believed to act as a lubricant or friction reducer.

A continuous filament nonwoven substrate 20 is unwound from a supply roll 22 and travels in the direction indicated by the arrow associated therewith as the supply roll 22 rotates in the direction of the arrows associated therewith. The nonwoven substrate 18 passes through a nip 24 of a S-roll arrangement 26 formed by the stack rollers 28 and 30.

The nonwoven substrate 20 may be formed by known continuous filament nonwoven extrusion processes, such as, for example, known solvent spinning or melt-spinning processes, and passed directly through the nip 16 without first being stored on a supply roll. The continuous filament nonwoven substrate 20 is preferably a nonwoven web of continuous melt-spun filaments formed by the spunbond process. The spunbond filaments may be formed from any melt-spinnable polymer, co-polymers or blends thereof. For example, the spunbond filaments may be formed from polyolefins, polyamides, polyesters, polyurethanes, A-B and A-B-A' block copolymers where A and A' are thermoplastic endblocks and B is an elastomeric midblock, and co-polymers of ethylene and at least one vinyl monomer such as, for example, vinyl acetates, unsaturated aliphatic monocarboxylic acids, and esters of such monocarboxylic acids. If the filaments are formed from a polyolefin such as, for example, polypropylene, the nonwoven substrate 20 may have a basis weight from about 3.5 to about 70 grams per square meter (gsm). More particularly, the nonwoven substrate 20 may have a basis weight from about 10 to about 35 gsm. The polymers may include additional materials such as, for example, pigments, antioxidants, flow promoters, stabilizers and the like.

One important characteristic of the nonwoven continuous filament substrate is that it has a total bond area of less than about 30 percent and a uniform bond density greater than about 100 bonds per square inch. For example, the nonwoven continuous filament substrate may have a total bond area from about 2 to about 30 percent (as determined by conventional optical microscopic methods) and a bond density from about 250 to about 500 pin bonds per square inch.

Figure 2:
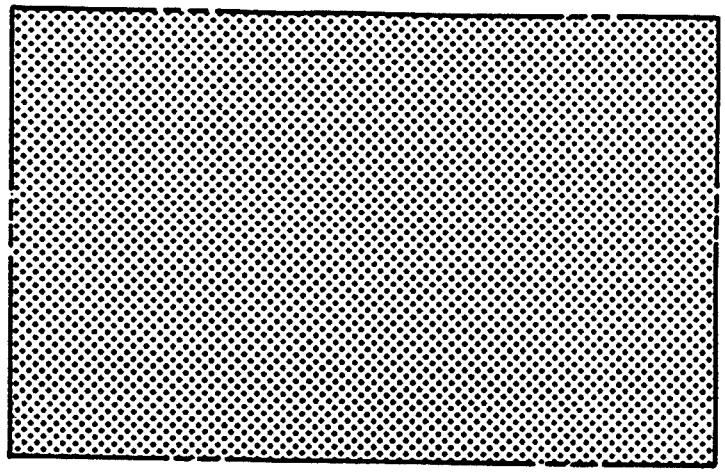
FIG. 2 is a plan view of an exemplary bond pattern.
Figure 3:
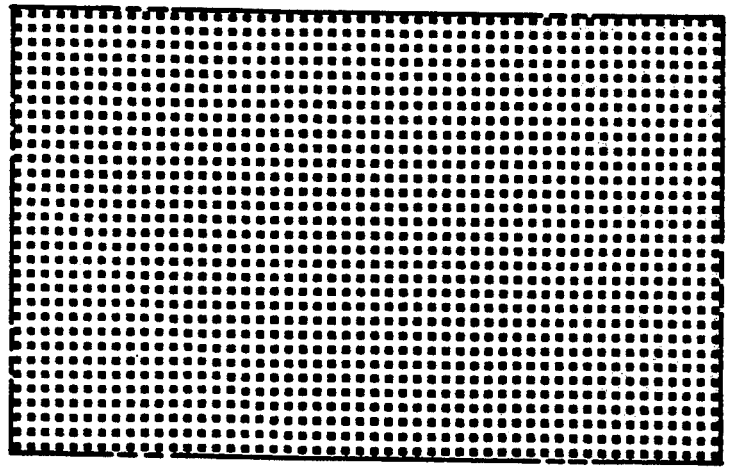
FIG. 3 is a plan view of an exemplary bond pattern.
Figure 4:
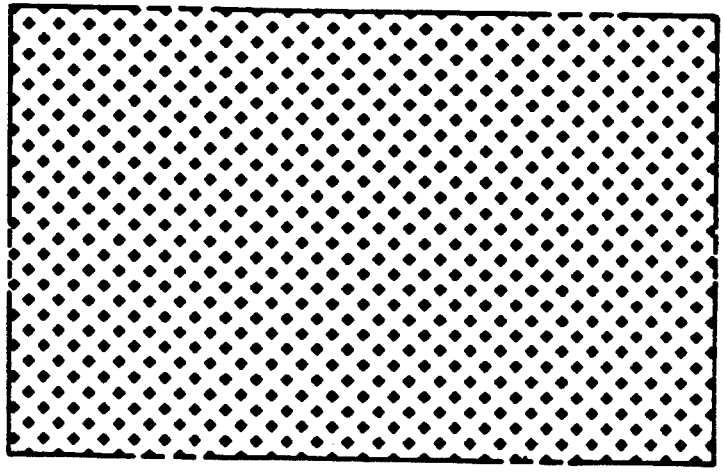
FIG. 4 is a plan view of an exemplary bond pattern.

Such a combination total bond area and bond density may be achieved by bonding the continuous filament substrate with a pin bond pattern having more than about 100 pin bonds per square inch which provides a total bond surface area less than about 30 percent when fully contacting a smooth anvil roll. Desirably, the bond pattern may have a pin bond density from about 250 to about 350 pin bonds per square inch and a total bond surface area from about 10 percent to about 25 percent when contacting a smooth anvil roll. An exemplary bond pattern is shown in FIG. 2 (714 pattern). That bond pattern has a pin density of about 306 pins per square inch. Each pin defines square bond surface having sides which are about 0.025 inch in length. When the pins contact a smooth anvil roller they create a total bond surface area of about 15.7 percent. High basis weight substrates generally have a bond area which approaches that value. Lower basis weight substrates generally have a lower bond area. FIG. 3 is another exemplary bond pattern (WW13 pattern). The pattern of FIG. 3 has a pin density of about 278 pins per square inch. Each pin defines a bond surface having 2 parallel sides about 0.035 inch long (and about 0.02 inch apart) and two opposed convex sides—each having a radius of about 0.0075 inch. When the pins contact a smooth anvil roller they create a total bond surface area of about 17.2 percent. FIG. 4 is another bond pattern which may be used. The patter of FIG. 4 has a pin density of about 103 pins per square inch. Each pin defines a square bond surface having sides which are about 0.043 inch in length. When the pins contact a smooth anvil roller they create a total bond surface area of about 16.5 percent.

Although pin bonding produced by thermal bond rolls is described above, the present invention contemplates any form of bonding which produces good tie down of the filaments with minimum overall bond area. For example, a combination of thermal bonding and latex impregnation may be used to provide desirable filament tie down with minimum bond area. Alternatively and/or additionally, a resin, latex or adhesive may be applied to the nonwoven continuous filament web by, for example, spraying or printing, and dried to provide the desired bonding.

The pulp fiber layer 18 is then laid on the nonwoven substrate 20 which rests upon a foraminous entangling surface 32 of a conventional hydraulic entangling machine. It is preferable that the pulp layer 18 is between the nonwoven substrate 20 and the hydraulic entangling manifolds 34. The pulp fiber layer 18 and nonwoven substrate 20 pass under one or more hydraulic entangling manifolds 34 and are treated with jets of fluid to entangle the pulp fibers with the filaments of the continuous filament nonwoven substrate 20. The jets of fluid also drive pulp fibers into and through the nonwoven substrate 20 to form the composite material 36.

Alternatively, hydraulic entangling may take place while the pulp fiber layer 18 and nonwoven substrate 20 are on the same foraminous screen (i.e., mesh fabric) which the wet-laying took place. The present invention also contemplates superposing a dried pulp sheet on a continuous filament nonwoven substrate, rehydrating the dried pulp sheet to a specified consistency and then subjecting the rehydrated pulp sheet to hydraulic entangling.

The hydraulic entangling may take place while the pulp fiber layer 18 is highly saturated with water. For example, the pulp fiber layer 18 may contain up to about 90 percent by weight water just before hydraulic entangling. Alternatively, the pulp fiber layer may be an air-laid or dry-laid layer of pulp fibers.

Hydraulic entangling a wet-laid layer of pulp fibers is desirable because the pulp fibers can be embedded into and/or entwined and tangled with the continuous filament substrate without interfering with "paper" bonding (sometimes referred to as hydrogen bonding) since the pulp fibers are maintained in a hydrated state. "Paper" bonding also appears to improve the abrasion resistance and tensile properties of the high pulp content composite fabric.

The hydraulic entangling may be accomplished utilizing conventional hydraulic entangling equipment such as may be found in, for example, in U.S. Pat. No. 3,485,706 to Evans, the disclosure of which is hereby incorporated by reference. The hydraulic entangling of the present invention may be carried out with any appropriate working fluid such as, for example, water. The working fluid flows through a manifold which evenly distributes the fluid to a series of individual holes or orifices. These holes or orifices may be from about 0.003 to about 0.015 inch in diameter. For example, the invention may be practiced utilizing a manifold produced by Honeycomb Systems Incorporated of Biddeford, Maine, containing a strip having 0.007 inch diameter orifices, 30 holes per inch, and 1 row of holes. Many other manifold configurations and combinations may be used. For example, a single manifold may be used or several manifolds may be arranged in succession.

In the hydraulic entangling process, the working fluid passes through the orifices at a pressures ranging from about 200 to about 2000 pounds per square inch gage (psig). At the upper ranges of the described pressures it is contemplated that the composite fabrics may be processed at speeds of about 1000 feet per minute (fpm) The fluid impacts the pulp fiber layer 18 and the nonwoven substrate 20 which are supported by a foraminous surface which may be, for example, a single plane mesh having a mesh size of from about 40×40 to about 100×100. The foraminous surface may also be a multi-ply mesh having a mesh size from about 50×50 to about 200×200. As is typical in many water jet treatment processes, vacuum slots 38 may be located directly beneath the hydro-needling manifolds or beneath the foraminous entangling surface 32 downstream of the entangling manifold so that excess water is withdrawn from the hydraulically entangled composite material 36.

Although the inventors should not be held to a particular theory of operation, it is believed that the columnar jets of working fluid which directly impact pulp fibers laying on the nonwoven continuous filament substrate work to drive those fibers into and partially through the matrix or nonwoven network of filaments in the substrate. When the fluid jets and pulp fibers interact with a nonwoven continuous filament web having the above-described bond characteristics (and a denier in the range of from about 5 microns to about 40 microns) the pulp fibers are also entangled with filaments of the nonwoven web and with each other. If the nonwoven continuous filament substrate is too loosely bonded, the filaments are generally too mobile to form a coherent matrix to secure the pulp fibers. On the other hand, if the total bond area of the substrate is too great, the pulp fiber penetration may be poor. Moreover, too much bond area will also cause a splotchy composite fabric because the jets of fluid will splatter, splash and wash off pulp fibers when they hit the large non-porous bond spots. The specified levels of bonding provide a coherent substrate which may be formed into a pulp fiber composite fabric by hydraulic entangling on only one side and still provide a strong, useful fabric as well as a composite fabric having desirable dimensional stability.

In one aspect of the invention, the energy of the fluid jets that impact the pulp layer and substrate may be adjusted so that the pulp fibers are inserted into and entangled with the continuous filament substrate in a manner that enhances the two-sidedness of the fabric. That is, the entangling may be adjusted to produce high pulp fiber concentration on one side of the fabric and a corresponding low pulp fiber concentration on the opposite side. Such a configuration may be particularly useful for special purpose wipers and for personal care product applications such as, for example, disposable diapers, feminine pads, adult incontinence products and the like. Alternatively, the continuous filament substrate may be entangled with a pulp fiber layer on one side and a different pulp fiber layer on the other side to create a composite fabric with two pulp-rich sides. In that case, hydraulically entangling both sides of the composite fabric is desirable.

After the fluid jet treatment, the composite fabric 36 may be transferred to a non-compressive drying operation. A differential speed pickup roll 40 may be used to transfer the material from the hydraulic needling belt to a non-compressive drying operation. Alternatively, conventional vacuum-type pickups and transfer fabrics may be used. If desired, the composite fabric may be wet-creped before being transferred to the drying operation. Non-compressive drying of the web may be accomplished utilizing a conventional rotary drum through-air drying apparatus shown in FIG. 1 at 42. The through-dryer 42 may be an outer rotatable cylinder 44 with perforations 46 in combination with an outer hood 48 for receiving hot air blown through the perforations 46. A through-dryer belt 50 carries the composite fabric 36 over the upper portion of the through-dryer outer cylinder 40. The heated air forced through the perforations 46 in the outer cylinder 44 of the through-dryer 42 removes water from the composite fabric 36. The temperature of the air forced through the composite fabric 36 by the through-dryer 42 may range from about 200° to about 500° F. Other useful through-drying methods and apparatus may be found in, for example, U.S. Pat. Nos. 2,666,369 and 3,821,068, the contents of which are incorporated herein by reference.

It may be desirable to use finishing steps and/or post treatment processes to impart selected properties to the composite fabric 36. For example, the fabric may be lightly pressed by calender rolls, creped or brushed to provide a uniform exterior appearance and/or certain tactile properties. Alternatively and/or additionally, chemical post-treatments such as, adhesives or dyes may be added to the fabric.

In one aspect of the invention, the fabric may contain various materials such as, for example, activated charcoal, clays, starches, and superabsorbent materials. For example, these materials may be added to the suspension of pulp fibers used to form the pulp fiber layer. These materials may also be deposited on the pulp fiber layer prior to the fluid jet treatments so that they become incorporated into the composite fabric by the action of the fluid jets. Alternatively and/or additionally, these materials may be added to the composite fabric after the fluid jet treatments. If superabsorbent materials are added to the suspension of pulp fibers or to the pulp fiber layer before water-jet treatments, it is preferred that the superabsorbents are those which can remain inactive during the wet-forming and/or water-jet treatment steps and can be activated later. Conventional superabsorbents may be added to the composite fabric after the water-jet treatments. Useful superabsorbents include, for example, a sodium polyacrylate superabsorbent available from the Hoechst Celanese Corporation under the trade name Sanwet IM-5000 P. Superabsorbents may be present at a proportion of up to about 50 grams of superabsorbent per 100 grams of pulp fibers in the pulp fiber layer. For example, the nonwoven web may contain from about 15 to about 30 grams of superabsorbent per 100 grams of pulp fibers. More particularly, the nonwoven web may contain about 25 grams of superabsorbent per 100 grams of pulp fibers.

Figure 5:
FIG. 5 is a photomicrograph of a cross section of an exemplary high pulp content nonwoven composite fabric.
Figure 6:
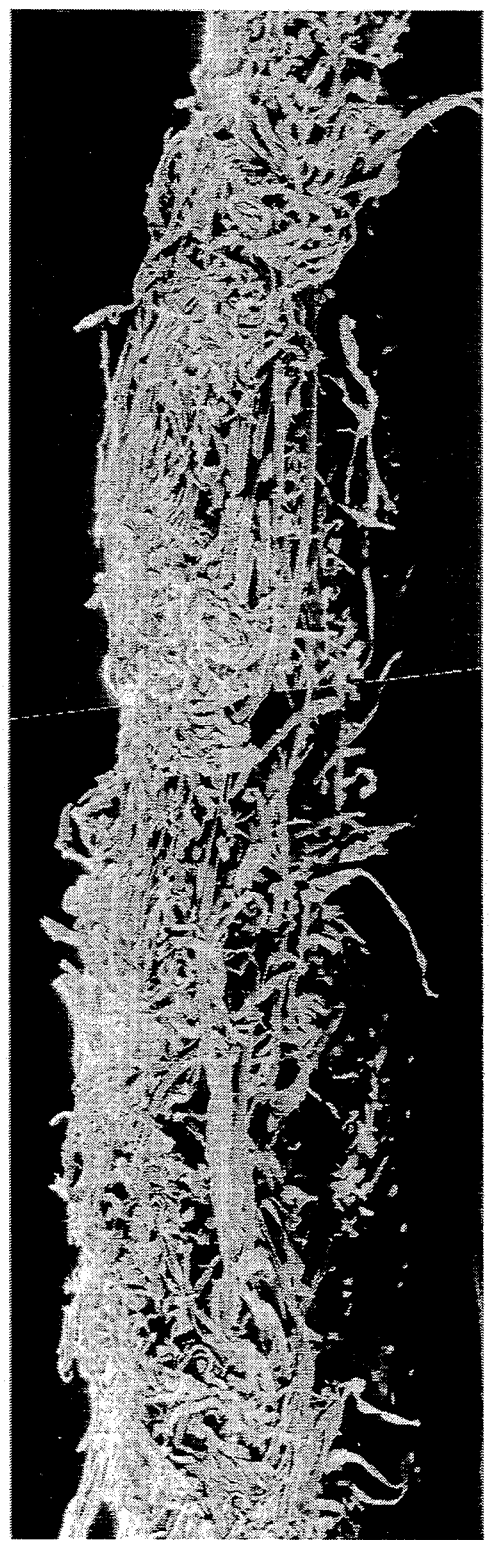
FIG. 6 is a photomicrograph of a cross section of an exemplary high pulp content nonwoven composite fabric after a post treatment step.

FIG. 5 is a 50.6X photomicrograph of a cross section of an exemplary high pulp content nonwoven composite fabric. FIG. 6 is a 50.6X photomicrograph of a cross-section of an exemplary high pulp content nonwoven composite fabric after a post treatment with cold embossing pattern rollers. As can be seen from FIGS. 5 and 6, the nonwoven composite fabrics contain a web of pulp fibers that are internally or integrally reinforced by a continuous filament nonwoven web. This eliminates the need for external reinforcing such as, for example, printed binders or adhesives. The internally or integrally reinforced material of the present invention also allows use of low-average fiber length pulp fibers. Such low-quality fibers can be treated with debonding agents to provide an even softer and more cloth-like material without decreases in strength and/or abrasion resistance which change the character of the material.

Figure 7:
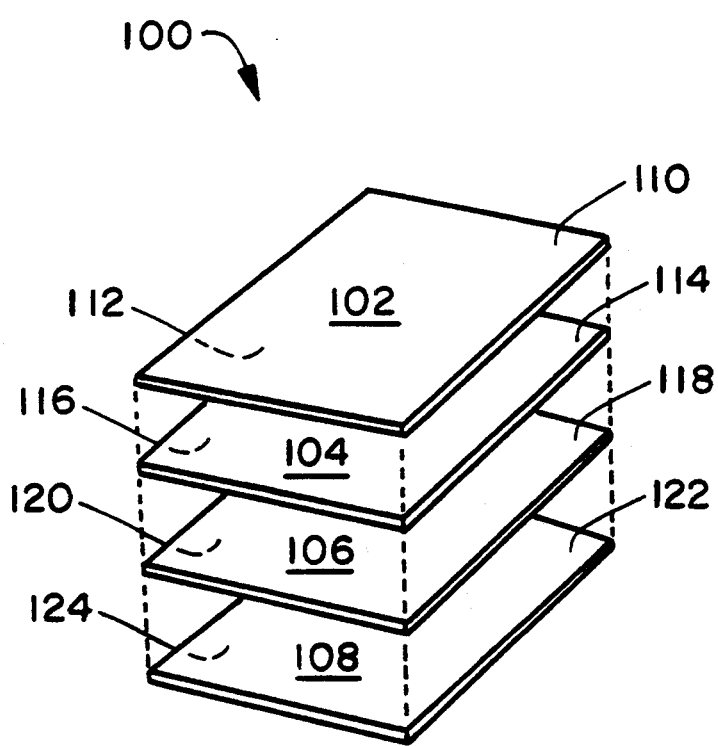
FIG. 7 is a representation of an exemplary absorbent structure that contains a high pulp content nonwoven composite fabric.

FIG. 7 is an exploded perspective view of an exemplary absorbent structure 100 which incorporates a high pulp content nonwoven composite fabric as a fluid distribution material. FIG. 7 merely shows the relationship between the layers of the exemplary absorbent structure and is not intended to limit in any way the various ways those layers may be configured in particular products. For example, an exemplary absorbent structure may have fewer layers or more layers than shown in FIG. 7. The exemplary absorbent structure 100, shown here as a multi-layer composite suitable for use in a disposable diaper, feminine pad or other personal care product contains four layers, a top layer 102, a fluid distribution layer 104, an absorbent layer 106, and a bottom layer 108. The top layer 102 may be a nonwoven web of melt-spun fibers or filaments, an apertured film or an embossed netting. The top layer 102 functions as a liner for a disposable diaper, or a cover layer for a feminine care pad or personal care product. The upper surface 110 of the top layer 102 is the portion of the absorbent structure 100 intended to contact the skin of a wearer. The lower surface 112 of the top layer 102 is superposed on the fluid distribution layer 104 which is a high pulp content nonwoven composite fabric. The fluid distribution layer 104 serves to rapidly desorb fluid from the top layer 102, distribute fluid throughout the fluid distribution layer 104, and release fluid to the absorbent layer 106. The fluid distribution layer has an upper surface 114 in contact with the lower surface 112 of the top layer 102. The fluid distribution layer 104 also has a lower surface 116 superposed on the upper surface 118 of an absorbent layer 106. The fluid distribution layer 104 may have a different size or shape than the absorbent layer 106. The absorbent layer 106 may be layer of pulp fluff, superabsorbent material, or mixtures of the same. The absorbent layer 106 is superposed over a fluid-impervious bottom layer 108. The absorbent layer 106 has a lower surface 120 which is in contact with an upper surface 122 of the fluid impervious layer 108. The bottom surface 124 of the fluid-impervious layer 108 provides the outer surface for the absorbent structure 100. In more conventional terms, the liner layer 102 is a topsheet, the fluid-impervious bottom layer 108 is a backsheet, the fluid distribution layer 104 is a distribution layer, and the absorbent layer 106 is an absorbent core. Each layer may be separately formed and joined to the other layers in any conventional manner. The layers may be cut or shaped before or after assembly to provide a particular absorbent personal care product configuration.

When the layers are assembled to form a product such as, for example, a feminine pad, the fluid distribution layer 104 of the high pulp content nonwoven composite fabric provides the advantages of reducing fluid retention in the top layer, improving fluid transport away from the skin to the absorbent layer 106, increased separation between the moisture in the absorbent core 106 and the skin of a wearer, and more efficient use of the absorbent layer 106 by distributing fluid to a greater portion of the absorbent. These advantages are provided by the improved vertical wicking and water absorption properties. In one aspect of the invention, the fluid distribution layer 104 may also serve as the top layer 102 and/or the absorbent layer 106. A particularly useful nonwoven composite fabric for such a configuration is one formed with a pulp-rich side and a predominantly continuous filament substrate side.

EXAMPLES

Tensile strength and elongation measurements of samples were made utilizing an Instron Model 1122 Universal Test Instrument in accordance with Method 5100 of Federal Test Method Standard No. 191A. Tensile strength refers to the maximum load or force (i.e., peak load) encountered while elongating the sample to break. Measurements of peak load were made in the machine and cross-machine directions for both wet and dry samples. The results are expressed in units of force (grams$_f$) for samples that measured 4 inches wide by 6 inches long.

The "elongation" or "percent elongation" of the samples refers to a ratio determined by measuring the difference between a sample's initial unextended length and its extended length in a particular dimension and dividing that difference by the sample's initial unextended length in that same dimension. This value is multiplied by 100 percent when elongation is expressed as a percent. The elongation was measured when the sample was stretched to about its breaking point.

Trapezoidal tear strengths of samples were measured in accordance with ASTM Standard Test D 1117-14 except that the tearing load is calculated as an average of the first and the highest peak loads rather than an average of the lowest and highest peak loads.

Particles and fibers shed from sample fabrics were measured by a Climet Lint test in accordance with INDA Standard Test 160.0-83 except that the sample size is 6 inch by 6 inch instead of 7 inch by 8 inch.

Water and oil absorption capacities of samples were measured in accordance with Federal Specification No. UU-T-595C on industrial and institutional towels and wiping papers. The absorptive capacity refers to the capacity of a material to absorb liquid over a period of time and is related to the total amount of liquid held by a material at its point of saturation. Absorptive capacity is determined by measuring the increase in the weight of a material sample resulting from the absorption of a liquid. Absorptive capacity may be expressed, in percent, as the weight of liquid absorbed divided by the weight of the sample by the following equation:

Total Absorptive Capacity = [(saturated sample weight − sample weight)/sample weight] × 100.

Water and oil wicking rates of samples were measured in accordance with TAPPI Method UM451. The wicking rate refers to the rate at which water is drawn in the vertical direction by a strip of an absorbent material.

The basis weights of samples were determined essentially in accordance with ASTM D-3776-9 with the following changes: 1) sample size was 4 inches × 4 inches square; and 2) a total of 9 samples were weighed.

The coefficient of friction was measured in accordance with ASTM 1894.

The drape stiffness of samples was measured in accordance with ASTM D1388 except that the sample size is 1 inch by 8 inches.

The cup crush test properties of samples were measured. The cup crush test evaluates fabric stiffness by measuring the peak load required for a 4.5 cm diameter hemispherically shaped foot to crush a 9"×9" piece of fabric shaped into an approximately 6.5 cm diameter by 6.5 cm tall inverted cup while the cup shaped fabric was surrounded by an approximately 6.5 cm diameter cylinder to maintain a uniform deformation of the cup shaped fabric. The foot and the cup were aligned to avoid contact between the cup walls and the foot which could affect the peak load. The peak load was measured while the foot was descending at a rate of about 0.25 inches per second (15 inches per minute) utilizing a Model FTD-G-500 load cell (500 gram range) available from the Schaevitz Company, Tennsauken, N.J.

When the bulk (i.e., thickness) of a sample was measured with an Ames Thickness Tester Model 3223 available from the B. C. Ames Company of Waltham, Mass., the thickness tester was equipped with a 5"×5" (25 inch$^2$) foot. The bulk of each sample was measured at a load of 182±5 grams.

When the bulk of a sample was measured with a Model 49-70 thickness tester available from TMI (Testing Machines Incorporated) of Amityville, N.Y., the thickness was measured using a 2-inch diameter circular foot at an applied pressure of about 0.2 pounds per square inch (psi). Thickness measurements reported for a $\frac{5}{8}$-inch diameter foot were conducted on a TMI Model 549-M thickness tester. The basis weight of the sample was determined essentially in accordance with ASTM D-3776-9.

Handle-O-Meter tests were performed on a Handle-O-Meter Model No 211-5 available from the Thwing-Albert Instrument Company. The tests were conducted in accordance with INDA Standard Test IST 90.0-75(R82) except that the sample size was 4"×4" instead of 8"×8".

Abrasion resistance testing was conducted on a Martindale Wear and Abrasion Tester Model No. 103 from Ahiba-Mathis, Charlotte, N.C. Tests were conducted according to ASTM D1175 using an applied pressure of 12 kilopascals (kPa). For the pulp-rich side of the composite, the abrasion test measured the number of cycles needed to form a ½ inch hole through the pulp-rich layer. For the continuous filament side of the fabric, samples were subjected to 150 cycles and then examined for the presence of surface fuzzing (fiber lofting), pilling, roping, or holes. The samples were compared to a visual scale and assigned a wear number from 1 to 5 with 5 indicating little or no visible abrasion and 1 indicating a hole worn through the sample.

EXAMPLE 1

A high pulp content nonwoven composite fabric was made by wet-forming a 73 gsm web of Northern softwood pulp fibers (Longlac 19 available from the Kimberly-Clark Corporation) and then transferring the web onto a 0.5 ounce per square yard (osy) (17 gsm) web of polypropylene spunbond filaments (formed as described, for example, in previously referenced U.S. Pat. Nos. 4,340,563 and 3,692,618). The spunbond filaments were bonded utilizing a pattern having approximately 103 pin bonds per square inch and which provides a maximum bond area of about 16.5 percent when contacted with a smooth anvil roll. The laminate, having a total basis weight of about 90 gsm, was hydraulically entangled into a composite material utilizing 4 manifolds. Each manifold was equipped with a jet strip having one row of 0.007 inch holes at a density of 30 holes per inch. Water pressure in the manifold was 650 psi (gage). The layers were supported on a 100 mesh stainless steel forming wire which travelled under the manifolds at a rate of about 20 fpm. The composite fabric was dried utilizing conventional through-air drying equipment. The peak load, peak strain (i.e., elongation) and peak Total Energy Absorbed were measured and are reported in Table 1.

EXAMPLE 2

A high pulp content nonwoven composite fabric was made by wet-forming a 70 gsm web of Northern softwood pulp fibers (Longlac 19 available from the Kimberly-Clark Corporation) and then transferring the web onto a 0.6 osy (20 gsm) web of polypropylene spunbond filaments. A wet-strength resin identified as Kymene 557 H available from the Hercules Chemical Company, Wilmington, Del., was added to the pulp fibers at a rate of 5 dry pounds per ton of dry fibers. The spunbond filaments were bonded utilizing a pattern having approximately 306 pin bonds per square inch and a maximum bond area of about 16 percent when contacted with a smooth anvil roll. The laminate, having a total basis weight of about 90 gsm, was hydraulically entangled into a composite material utilizing 4 manifolds. Each manifold was equipped with a jet strip having one row of 0.007 inch holes at a density of 30 holes per inch. Water pressure in the manifolds was about 700 psi (gage). The layers were supported on a 100 mesh stainless steel forming wire as they passed under the manifolds at a rate of about 30 fpm. The composite fabric was dried by being passed over steam can rollers. The dried fabric was cold embossed. Physical properties of the composite fabric were measured and are reported in Table 1.

EXAMPLE 3

A high pulp content nonwoven composite fabric was made by wet-forming a 76 gsm web of Northern softwood pulp fibers (Longlac 19 available from the Kimberly-Clark Corporation) and then transferring the web onto a 0.4 osy (14 gsm) web of polypropylene spunbond filaments. A wet-strength resin (Kymene 557 H available from the Hercules Chemical Company) was added to the pulp fibers at a rate of 5 dry pounds per ton of dry fibers. Also, a de-bonder (Quaker 2008 available from the Quaker Chemical Company, Conshohocken, Pa.) was added to the pulp fibers at a rate of about 90 dry pounds per ton of dry fibers. The spunbond filaments were bonded utilizing a pattern having approximately 306 pin bonds per square inch and a maximum bond area of about 16 percent when contacted with a smooth anvil roll. The laminate, having a total basis weight of about 90 gsm, was hydraulically entangled into a composite material utilizing the equipment and procedures described in Example 2. The composite fabric was dried by being passed over steam can rollers. The dried fabric was cold embossed. Physical properties of the composite fabric were measured and are reported in Table 1.

EXAMPLE 4

A high pulp content nonwoven composite fabric was made by wet-forming a 73 gsm web of Northern softwood pulp fibers (Longlac 19 available from the Kimberly-Clark Corporation) and then transferring the web onto a 0.5 osy (17 gsm) web of polypropylene spunbonded filaments. The spunbond filaments were bonded utilizing a pattern having approximately 103 pin bonds per square and a maximum bond area of about 16.5 percent when contacted with a smooth anvil roll. The laminate, having a total basis weight of about 90 gsm, was hydraulically entangled into a composite material utilizing 3 manifolds at the same conditions given in Example 1. An adhesive available from the Rohm & Haas Company, Philadelphia, Pa., under the trade name Rhoplex ® B was sprayed onto the composite fabric at a rate of about 0.9 gsm (to make up about 1 percent, by weight, of the 90 gsm composite). The composite fabric was then dried utilizing conventional through-air drying equipment. The peak load, peak strain (i.e., elongation) and peak Total Energy Absorbed were measured and are reported in Table 1.

TABLE 1

Examples 1–4
GRAB TENSILE:

Example 1

| PEAK LOAD (LB) | | | | ELONGATION (%) | | | | TOTAL ENERGY ABSORBED (IN LB/IN) | | | |
|---|---|---|---|---|---|---|---|---|---|---|---|
| MDD | CDD | MDW | CDW | MDD | CDD | MDW | CDW | MDD | CDD | MDW | CDW |
| 27.2 | 24.8 | 23.2 | 22.9 | 19 | 63 | 43 | 74 | 11.2 | 28.2 | 16.6 | 27.4 |

Example 2

| PEAK LOAD (LB) | | | | ELONGATION (%) | | | | TOTAL ENERGY ABSORBED (IN LB/IN) | | | |
|---|---|---|---|---|---|---|---|---|---|---|---|
| MDD | CDD | MDW | CDW | MDD | CDD | MDW | CDW | MDW | CDW | MDW | CDW |

TABLE 1-continued

| 25.3 | 23.6 | 22.9 | 2.10 | 31 | 56 | 44 | 65 | 14.7 | 20.6 | 17.5 | 21.6 |

| TRAP TEAR (LB) | | WATER WICKING (CM) | | | | | | | | WATER CAPACITY | | OIL CAPACITY (CM) | |
|---|---|---|---|---|---|---|---|---|---|---|---|---|---|
| | | MD | | | | CD | | | | | | | |
| MDW | CDW | 15 (sec) | 30 | 45 | 60 | 15 (sec) | 30 | 45 | 60 | % | G/Ft | % | G/Sq.Ft. |
| 5.7 | 5.2 | 2.6 | 4.1 | 4.7 | 5.5 | 1.9 | 2.7 | 3.4 | 4.0 | 412 | 35 | 221 | 19.5 |

| HANDLE-O-METER (G) | | CUP CRUSH PLOAD (G) | ENERGY | TMI BULK 2" - FOOT (INCH) |
|---|---|---|---|---|
| MD | CD | | | |
| 101 | 45 | 442 | 10299 | .021 |

Wet Martindale Abrasion: Pulp side - 450 cycles to ⅛" hole
SB Side - Ranking - 2 (1 = Poor, 5 = No Abrasion)

Example 3

| PEAK LOAD (LB) | | | | ELONGATION (%) | | | | TOTAL ENERGY ABSORBED (IN LB/IN) | | | |
|---|---|---|---|---|---|---|---|---|---|---|---|
| MDD | CDD | MDW | CDW | MDD | CDD | MDW | CDD | MDW | CDW | MDW | CDW |
| 10.9 | 8.5 | 10.8 | 7.8 | 37 | 49 | 49 | 64.7 | 7.1 | 6.9 | 9.0 | 8.1 |

| TRAP TEAR (LB) | | WATER WICKING (CM) | | | | | | | | WATER CAPACITY | | OIL CAPACITY (CM) | |
|---|---|---|---|---|---|---|---|---|---|---|---|---|---|
| | | MD | | | | CD | | | | | | | |
| MDW | CDW | 15 | 30 | 45 | 60 | 15 | 40 | 45 | 60 | % | G/Ft. 2 FT | % | G/Sq. Ft. |
| 3.8 | 3.4 | 2.3 | 3.2 | 3.8 | 4.4 | 2.0 | 2.8 | 3.2 | 3.7 | 564 | 50 | 266 | 23.5 |

| HANDLE-O-METER (G) | | CUP CRUSH PLOAD (G) | ENERGY | TMI BULK 2" - FOOT (INCH) |
|---|---|---|---|---|
| MD | CD | | | |
| 59 | 25 | 315 | 5139 | .025 |

Example 4

| PEAK LOAD (LB) | | | | ELONGATION (%) | | | | TOTAL ENERGY ABSORBED (IN LB/IN) | | | |
|---|---|---|---|---|---|---|---|---|---|---|---|
| MDD | CDD | MDW | CDW | MDD | CDD | MDW | CDW | MDD | CDD | MDW | CDW |
| 21.1 | 23.5 | 18.4 | 22.9 | 24 | 64 | 56 | 84 | 11.5 | 26.3 | 18.2 | 33.9 |

EXAMPLE 5

A high pulp content nonwoven composite fabric was made by wet-forming a 72 gsm web of Northern softwood pulp fibers (Longlac 19 available from the Kimberly-Clark Corporation) and then transferring the web onto a 0.5 osy (17 gsm) web of polypropylene spunbond filaments. The spunbond filaments were bonded utilizing a pattern having approximately 103 pin bonds per square inch and a total bond area of about 16.5 percent when contacted with a smooth anvil roll. The laminate, having a total basis weight of about 89 gsm, was hydraulically entangled into a composite material utilizing 4 manifolds. Each manifold was equipped with a jet strip having one row of 0.007 inch holes at a density of 30 holes per inch. Water pressure in the manifolds was about 650 psi (gage). The layers were supported on a 100 mesh stainless steel forming wire which passed under the manifolds at a rate of about 20 fpm. The composite fabric was dried utilizing conventional through-air drying equipment. Physical properties and absorbency characteristics of the fabric were measured and are reported in Table 2.

EXAMPLE 6

A high pulp content nonwoven composite fabric was formed as described in Example 5 except that the fabric had a basis weight of about 82 gsm and was mechanically softened utilizing intermeshed grooved rolls. Physical properties and absorbency characteristics of the fabric were measured and are reported in Table 2.

EXAMPLE 7

A high pulp content nonwoven composite fabric was formed as described in Example 5 except that the fabric had a basis weight of about 86 gsm and was cold embossed with a floral pattern. Physical properties and absorbency characteristics of the fabric were measured and are reported in Table 2.

EXAMPLE 8

An externally reinforced Wypall ® 5700 wiper available from the Scott Paper Company, Philadelphia, Pa., was tested for physical properties and absorbency characteristics. The wiper had a basis weight of about 85 gsm and contained about 84 percent, by weight, of a creped pulp sheet and about 16 percent by weight of an adhesive printed onto both sides of the pulp sheet. The results of the testing are reported in Table 2.

EXAMPLE 9

A high pulp content nonwoven composite fabric was made by forming a 73 gsm web from a mixture of about 70 percent, by weight, Northern softwood pulp fibers (Longlac 19 available from the Kimberly-Clark Corporation) and 30 percent, by weight, Southern softwood pulp fibers (Brunswick pulp available from the Georgia Pacific Corporation, Atlanta, Ga.) and then transferring the web onto a 0.4 osy (14 gsm) web of polypropylene spunbond filament. The spunbond filaments were bonded utilizing a pattern having approximately 278 pin bonds per square inch which provides a total bond area of about 17.2 percent when contacted with a smooth anvil roll. The laminate, having a total basis weight of about 87 gsm, was hydraulically entangled into a composite material utilizing 3 manifolds. Each manifold was equipped with a jet strip having one row of 0.007 inch holes at a density of 30 holes per inch. Water pressure in the manifolds was about 1050 psi (gage). The layers were supported on a 100 mesh stainless steel forming wire which passed under the manifolds at a rate of about 100 fpm. The composite fabric was dried utilizing conventional steam-can drying equipment. The fabric was cold embossed with the pattern shown in FIG. 8. Physical properties and absorbency characteristics of the fabric were measured and are reported in Table 4.

EXAMPLE 10

A high pulp content nonwoven composite fabric was made by forming a 70 gsm web from Northern softwood pulp fibers (Longlac 19 available from the Kimberly-Clark Corporation) and then transferring the web onto a 0.5 osy (17 gsm) web of spunbond filaments. The spunbond filaments were bonded utilizing the pattern described in Example 9. The laminate, having a total basis weight of about 87 gsm, was hydraulically entangled into a composite material as described in Example 9 except that water pressure at the manifolds was about 1100 psi (gage). The composite fabric was dried utilizing conventional steam-can drying equipment. The fabric was cold embossed with the pattern shown in FIG. 8. Physical properties and absorbency characteristics of the fabric were measured and are reported in Table 3.

EXAMPLE 11

A high pulp content nonwoven composite fabric was made by forming a 73 gsm web from a mixture of about 30 percent, by weight, Northern softwood pulp fibers (Longlac 19 available from the Kimberly-Clark Corporation) and about 70 percent, by weight, secondary fibers (BJ de-inked secondary fiber pulp available from the Ponderosa Pulp Products—a division of Ponderosa Fibers of America, Atlanta, Ga.) and then transferring the web onto a 0.4 osy (14 gsm) web of polypropylene spunbond filaments. The spunbond filaments were bonded utilizing the pattern described in Example 9. The laminate, having a total basis weight of about 87 gsm, was hydraulically entangled into a composite material as described in Example 9 except that 4 manifolds were used. The composite fabric was dried utilizing conventional steam-can drying equipment. The fabric was cold embossed with the pattern shown in FIG. 8. Physical properties and absorbency characteristics of the fabric were measured and are reported in Table 3.

EXAMPLE 12

A high pulp content nonwoven composite fabric was made as described in Example 10 except that the pulp layer was formed from a mixture of about 70 percent, by weight, Northern softwood pulp fibers (Longlac 19 available from the Kimberly-Clark Corporation) and about 30 percent, by weight, secondary fibers (BJ de-inked secondary fiber pulp available from the Ponderosa Pulp Products). Physical properties and absorbency characteristics of the fabric were measured and are reported in Table 3.

TABLE 2

| | Examples 5-8 | | | |
|---|---|---|---|---|
| | EXAMPLE 5 | EXAMPLE 6 | EXAMPLE 7 | EXAMPLE 8 |
| BASIS WEIGHT (GSM) | 89 | 82 | 86 | 85 |
| GRAB TENSILE - LOAD | | | | |
| MDD (lbs.) | 23.5 (1.1) | 21.0 (2.7) | 20.4 (1.5) | 7.5 (0.5) |
| CDD | 19.6 (2.8) | 16.8 (0.5) | 18.0 (1.9) | 5.7 (0.2) |
| MDW | 20.9 (1.1) | 17.8 (2.0) | 19.5 (1.6) | 5.6 (0.4) |
| CDW | 18.4 (1.0) | 21.7 (0.8) | 19.5 (1.8) | 4.3 (0.3) |
| GRAB TENSILE - % ELONG | | | | |
| MDD (%) | 23 (1) | 21 (4) | 25 (2) | 38 (1) |
| CDD | 62 (8) | 51 (4) | 53 (3) | 18 (1) |
| MDW | 40 (5) | 46 (5) | 44 (4) | 42 (0.5) |
| CDW | 74 (7) | 75 (3) | 79 (13) | 25 (1) |
| GRAB TENSILE - ENERGY | | | | |
| MDD (in lbs.) | 11.5 (1.2) | 9.2 (2.9) | 9.2 (1.4) | 3.4 (0.3) |
| CDD | 20.1 (5.8) | 13.6 (1.4) | 15.6 (2.4) | 1.5 (0.0) |
| MDW | 16.0 (1.6) | 14.3 (2.5) | 15.4 (2.7) | 2.3 (0.2) |
| CDW | 22.2 (3.2) | 25.8 (8.3) | 24.1 (5.6) | 1.5 (0.2) |
| TRAP TEAR | | | | |
| MDD (lbs.) | 5.9 (0.6) | 5.1 (0.5) | 5.7 (0.3) | 0.8 |
| CDD | 5.9 (0.7) | 4.7 (0.3) | 4.8 (0.3) | 0.6 |
| MDW | 7.9 (1.7) | 6.4 (0.5) | 5.6 (0.6) | — |
| CDW | 5.3 (1.2) | 5.6 (1.7) | 5.2 (0.2) | — |
| WATER CAPACITY | | | | |
| (%) | 536 | 551 | 555 | 738 |
| (G/Sq. Ft.) | 48 | 48 | 46 | 58 |
| WATER WICKING - MD | | | | |
| 15 Sec. (CM) | 3.1 | 3.6 | 3.3 | 1.2 |
| 30 Sec. (CM) | 5.1 | 5.0 | 4.6 | 2.0 |
| 45 Sec. (CM) | 6.0 | 6.2 | 5.7 | 2.5 |
| 60 Sec. (CM) | 6.6 | 6.8 | 6.3 | 3.0 |
| WATER WICKING - CD | | | | |
| 15 Sec. (CM) | 2.8 | 2.8 | 2.7 | 2.0 |
| 30 Sec. (CM) | 4.0 | 4.0 | 3.9 | 3.0 |
| 45 Sec. (CM) | 4.9 | 5.1 | 4.9 | 3.5 |
| 60 Sec. (CM) | 5.6 | 5.7 | 5.6 | 4.0 |
| OIL CAPACITY | | | | |
| (%) | 375 | 357 | 352 | 496 |
| (G/Sq. Ft.) | 31 | 31 | 30 | 40 |
| OIL WICKING - MD | | | | |
| 15 Sec. (CM) | 1.9 | 0.9 | 0.7 | 0.5 |
| 30 Sec. (CM) | 2.0 | 1.3 | 1.0 | 1.0 |
| 45 Sec. (CM) | 2.2 | 1.5 | 1.3 | 1.3 |
| 60 Sec. (CM) | 2.4 | 1.8 | 1.5 | 1.5 |
| OIL WICKING - CD | | | | |
| 15 Sec. (CM) | 0.7 | 0.7 | 0.6 | 0.5 |

TABLE 2-continued

| | Examples 5-8 | | | |
|---|---|---|---|---|
| | EXAMPLE 5 | EXAMPLE 6 | EXAMPLE 7 | EXAMPLE 8 |
| 30 sec. (CM) | 1.0 | 1.0 | 0.9 | 1.0 |
| 45 sec. (CM) | 1.3 | 1.3 | 1.2 | 1.0 |
| 60 Sec. (CM) | 1.5 | 1.4 | 1.5 | 1.0 |
| BULK - TMI (5.8" Foot) | | | | |
| DRY (MIL) | 216 (5) | 160 (5) | 169 (1) | |
| WET | 141 (5) | 117 (2) | 129 (2) | |
| AMES BULK | | | | |
| DRY (IN) | 0.032 | 0.037 | 0.038 | 0.036 |
| WET | 0.030 | 0.031 | 0.031 | 0.028 |
| DRAPE STIFFNESS | | | | |
| MD (CM) | 7.2 (0.8) | 4.2 (0.3) | 3.6 (0.5) | 2.5 |
| CD | 4.4 (0.4) | 2.6 (0.6) | 3.6 (0.3) | 4.1 |
| CLIMET LINT | | | | |
| 0.5-10 Micron | 2236 (713) | 1868 (331) | 2638 (854) | 390 |
| >10 Micron | 1 (0) | 0.7 (0.6) | 2 (1) | 0.2 |

TABLE 3

| | Examples 9-12 | | | |
|---|---|---|---|---|
| | EXAMPLE 9 | EXAMPLE 10 | EXAMPLE 11 | EXAMPLE 12 |
| BASIS WEIGHT (GSM) | 87 | 87 | 99 | 103 |
| Grab Tensile Peak Load | | | | |
| MDD (Lbs.) | 12.2 (1.4) | 13.6 (1.4) | 16.5 (6.6) | 15.2 (0.9) |
| CDD | 8.9 (0.5) | 9.6 (1.1) | 7.8 (1.0) | 7.9 (0.6) |
| MDW | 8.6 (1.8) | 13.6 (1.3) | 10.7 (0.8) | 11.8 (0.8) |
| CDW | 7.2 (1.4) | 7.8 (1.5) | 6.1 (0.5) | 6.3 (0.4) |
| Grab Tensile Percent Elongation | | | | |
| MDD (%) | 40 (6.7) | 39 (3.9) | 20 (5.5) | 22 (4.8) |
| CDD | 68 (4.8) | 58 (7.8) | 42 (7.2) | 40 (4.4) |
| MDW | 30 (9.9) | 55 (11.1) | 25 (1.7) | 26 (3.0) |
| CDW | 62 (11.6) | 58 (15.0) | 59 (4.7) | 54 (5.8) |
| Grab Tensile Energy | | | | |
| MDD (Lbs.) | 0.8 (0.2) | 0.8 (0.2) | 0.4 (0.2) | 0.5 (0.2) |
| CDD | 0.9 (0.1) | 0.8 (0.2) | 0.5 (0.1) | 0.5 (0.1) |
| MDW | 0.4 (0.2) | 1.2 (0.2) | 0.4 (0.1) | 0.4 (0.1) |
| CDW | 0.7 (0.2) | 0.7 (0.3) | 0.5 (0.1) | 0.5 (0.1) |
| Trap Tear | | | | |
| MDD (lbs.) | 5.5 (1.8) | 4.3 (1.0) | 3.0 (0.8) | 3.1 (0.3) |
| CDD | 2.5 (0.8) | 3.3 (1.3) | 1.9 (0.9) | 2.2 (0.8) |
| MDW | 3.8 (1.2) | 5.0 (1.3) | | |
| CDW | 2.7 (0.3) | 3.4 (1.4) | | |
| WATER CAPACITY | | | | |
| Percent (%) | 541 (4.0) | 540 (2.0) | 458 (14.1) | 483 (7.6) |
| G/SF | 46 (0.8) | 42 (0.3) | 42 (0.9) | 45 (1.2) |
| WATER WICKING - MD | | | | |
| 15 SEC (CM) | 2.2 | 2.0 | 2.5 | 2.3 |
| 30 SEC (CM) | 3.1 | 2.7 | 3.6 | 3.3 |
| 45 SEC (CM) | 3.7 | 3.6 | 4.4 | 4.1 |
| 60 SEC (CM) | 4.4 | 4.1 | 4.9 | 4.7 |
| WATER WICKING - CD | | | | |
| 15 SEC (CM) | 1.7 | 1.8 | 1.9 | 1.9 |
| 30 SEC (CM) | 2.4 | 2.3 | 2.6 | 2.5 |
| 45 SEC (CM) | 3.0 | 2.6 | 3.3 | 3.3 |
| 60 SEC (CM) | 3.5 | 3.5 | 3.7 | 3.9 |
| OIL CAPACITY | | | | |
| % | 331 (11.0) | 359 (2.0) | 290 (8.7) | 314 (7.6) |
| G/SF | 28 (0.9) | 28 (0.1) | 27 (0.6) | 30 (1.2) |
| BULK - TMI (2") | | | | |
| Dry (.001") | 23.4 (0.5) | 22.0 (0.2) | 23.3 (0.8) | 23.3 (0.2) |
| Wet | | | | |
| CLIMET LINT | | | | |
| >5 μm | 7 (3) | 8 (4) | 5 (3) | 7 (4) |
| 0.5 μm-5 μm | 519 (130) | 592 (214) | 3257 (676) | 2628 (668) |
| HANDLE-O-METER | | | | |
| MD | 78 (20) | 76 (17) | 108 (0) | 107 (1) |
| CD | 21 (5) | 19 (6) | 35 (11) | 36 (9) |
| CUP CRUSH | | | | |
| Grams | 334 (68) | 358 (37) | 442 (0) | 419 (39) |
| Energy | 6663 (1592) | 6696 (757) | 9193 (664) | 8443 (1662) |
| WET MARTINDALE ABRASION PULP SIDE # of Cycles to ¼" hole | 91 | 350 | 350 | 350 |

TABLE 3-continued

| | Examples 9-12 | | | |
|---|---|---|---|---|
| | EXAMPLE 9 | EXAMPLE 10 | EXAMPLE 11 | EXAMPLE 12 |
| WET MARTINDALE ABRASION SPUN-BOND SIDE RUM 150 CYCLES Values are 1 to 5 | 4.5 | 4.5 | 4.75 | 5 |

EXAMPLE 13

A thin absorbent structure having a wettable cover was made utilizing top layer of 27 gsm polypropylene spunbonded polypropylene treated with about 0.3% of TRITON® X102 (Octylphynoxypolyethoxyethanol nonionic surfactant) available from the Rohm and Haas Company; an intermediate layer of a high pulp content nonwoven composite fabric having a basis weight of about 110 gsm (about 20 gsm spunbond polypropylene bonded with the pattern of FIG. 4 and about 90 gsm Northern softwood pulp); and an absorbent core of 1) a C-folded double layer of a laminate composite having two 52 gsm plies of air-laid tissue sandwiching a 75 gsm layer of polyacrylate super absorbent particulates and 2) a 168 gsm longitudinally scored wood pulp fiber blotter paper. Each layer measured about 1.25 inches by about 8 inches. The layers were superposed into an absorbent structure that was held on a flat, horizontal surface.

Another thin absorbent structure was made from the same cover material and absorbent core but contained an intermediate layer of a 60 gsm nonwoven web of meltblown polypropylene fibers treated with about 1 percent, by weight, of a dioctyl sodium sulfosuccinate surfactant.

The two structures were tested to determine how quickly each could distribute and absorb an artificial menstrual fluid obtained from the Kimberly-Clark Corporation's Analytical Laboratory, Neenah, Wis. This fluid had a viscosity of about 17 centipoise at room temperature (about 73° F.) and a surface tension of about 53 dynes/centimeter.

Approximately 10 cm³ of the fluid was dripped onto the center of each structure at a constant rate of 10 cm³ per minute from a height of about 1 cm. About one hour after the insult, the length of the stain on the longitudinal axis of the fluid distribution layer was measured. A larger stain length is more desirable because it shows better dispersion of the fluid. The results of this test are reported in Table 4.

TABLE 4

| Intermediate Layer | Stain length (cm) |
|---|---|
| 110 gsm high pulp content nonwoven composite fabric | 13.6 |
| 60 gsm meltblown polypropylene | 12.0 |

EXAMPLE 14

The thin absorbent structures of Example 13 were tested to determine how rapidly each would absorb 8 cm³ of the artificial menstrual fluid utilizing a test apparatus which consisted of 1) a Lucite® block and 2) a flat, horizontal test surface.

Figure 8:
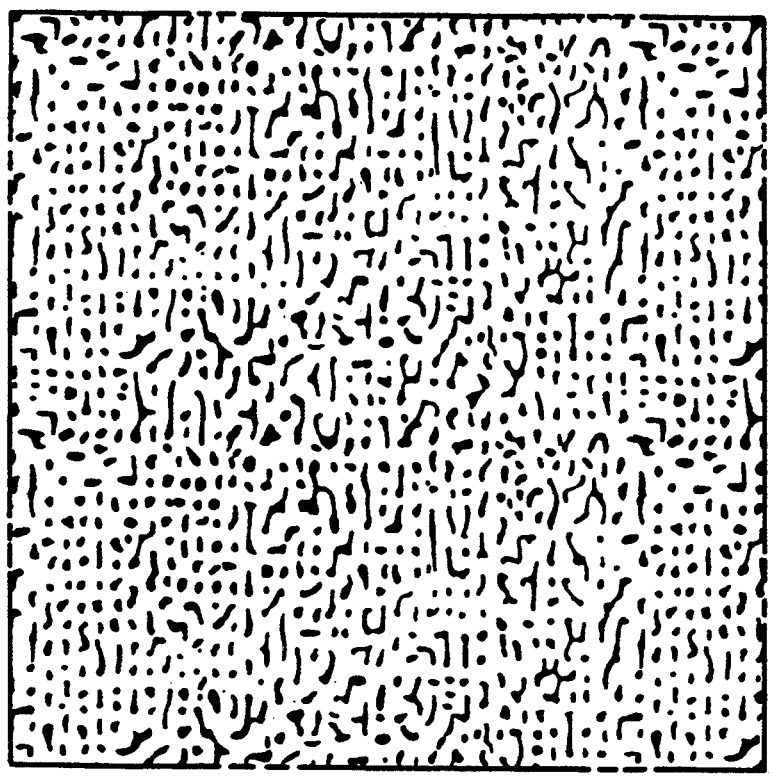
FIG. 8 is a plan view of an exemplary embossing pattern.
Figure 9:
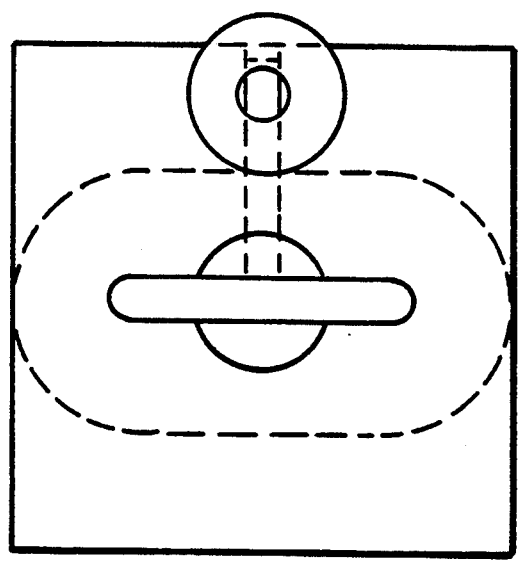
FIG. 9 is a top view of a test apparatus for measuring the rate which an absorbent structure absorbs a liquid.
Figure 10:
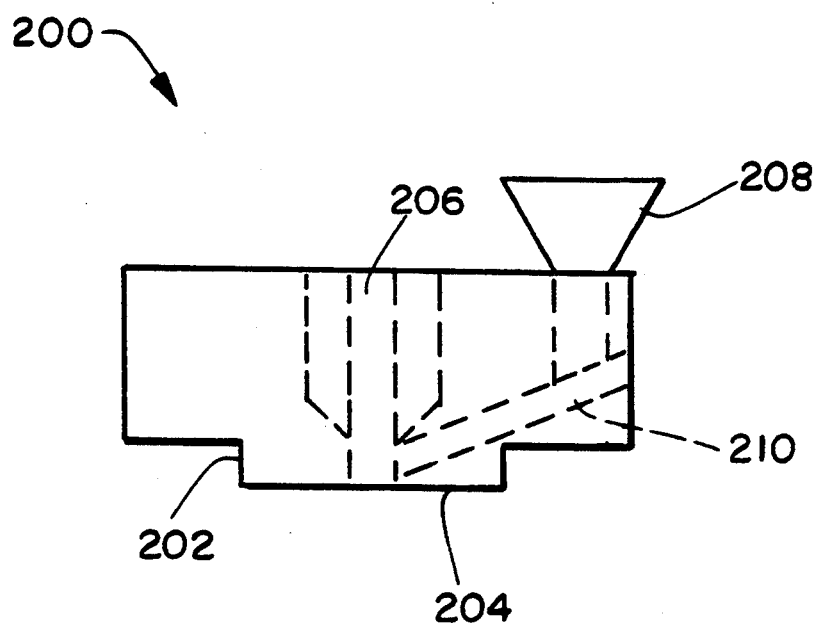
FIG. 10 is a cross-sectional view of a test apparatus for measuring the rate which an absorbent structure absorbs a liquid.

FIG. 8 is a plan view of the Lucite® block. FIG. 9 is a sectional view of the Lucite® block. The block 200 has a base 202 which protrudes from the bottom of the block. The base 202 has a flat surface 204 which is approximately 2,875 inches long by 1.5 inches wide that forms the bottom of the block 200. An oblong opening 206 (about 1.5 inches long by about 0.25 inch wide) is located in the center of the block and extends from the top of the block to the base 202 of the block. When the bottom of the opening 206 is obstructed, the opening 206 can hold more than about 10 cm³ of fluid. A mark on the opening 206 indicates a liquid level of about 2 cm³. A funnel 208 on the top of the block feeds into a passage 210 which is connected to the oblong opening 206. Fluid poured down the funnel 208 passes through the passage 210 into the oblong opening 206 and out onto a test sample underneath the block.

Each sample was tested by placing it on a flat, horizontal test surface and then putting the flat, projecting base of the block on top of the sample so that the long dimension of the oblong opening was parallel to the long dimension of the sample and centered between the ends and sides of the sample. The weight of the block was adjusted to about 162 grams so that so that the block rested on the structure with a pressure of about 7 grams/cm₂ (about 1 psi). A stopwatch was started as approximately ten (10) cm³ of the fluid was dispensed into the funnel from a Repipet (catalog No. 13-687-20; Fischer Scientific Company). The fluid filled the oblong opening of the block and the watch was stopped when the meniscus of the fluid reached the 2 cm³ level indicating that 8 cm³ of fluid was absorbed. The results of this test are reported in Table 5.

TABLE 5

| Intermediate Layer | 8 cm³ Time (sec) |
|---|---|
| 110 gsm high pulp content nonwoven composite fabric | 78 |
| 60 gsm meltblown polypropylene | 96 |

EXAMPLE 15

A thick absorbent structure having an embossed net cover was made utilizing top layer of an embossed netting having a basis weight of about 45 gsm and an open area of about 35 to about 40%; an intermediate layer of a high pulp content nonwoven composite fabric having a basis weight of about 110 gsm (about 25 gsm spunbond polypropylene bonded with the pattern of FIG. 4 and about 90 gsm Northern softwood pulp); and an absorbent core of an approximately 760 gsm batt of Southern softwood wood pulp fluff (pulp fluff #54 from Kimberly-Clark Corporation's Coosa River plant). The intermediate layer measured about 1.25 inches by 8.5 inches. The absorbent core measured about 2.5 inches by about 7.5 inches and the cover was large enough to wrap the entire structure.

Another thick absorbent structure was made from the same cover material and absorbent core but with an intermediate layer of a 60 gsm nonwoven web of meltblown polypropylene fibers treated with a surfactant as described in Example 13.

The two structures were tested to determine how quickly each could distribute 10 cm³ of an artificial menstrual fluid according to the procedure described in Example 13. The results are reported in Table 6.

TABLE 6

| Intermediate Layer | Stain length (cm) |
|---|---|
| 110 gsm high pulp content nonwoven composite fabric | 14.0 |
| 60 gsm meltblown polypropylene | 9.6 |

EXAMPLE 16

The absorbent structures of Example 15 were tested according to the procedure described in Example 14 to determine how quickly each absorbed 8 cm³ of an artificial menstrual fluid. The results are reported in Table 7.

TABLE 7

| Intermediate Layer | 8 cm³ Time (sec) |
|---|---|
| 110 gsm high pulp content nonwoven composite fabric | 16.8 |
| 60 gsm meltblown polypropylene | 16.5 |

As can be seen from Tables 4 and 6, the absorbent structures containing the 110 gsm high pulp content nonwoven composite fabric of the present invention were able to distribute the test fluid better than the absorbent structures containing the surfactant-treated meltblown polypropylene fluid distribution layer. Tables 5 and 7 show that the absorbent structures containing the 110 gsm high pulp content nonwoven composite fabric of the present invention were able to absorb the test fluid as well as or better than the absorbent structures containing the surfactant-treated meltblown polypropylene fluid distribution layer.

EXAMPLE 17

A high pulp content nonwoven composite fabric was made by wet-forming a 76 gsm web from a mixture of about 30 percent, by weight, Northern softwood pulp fibers (Longlac 19 available from the Kimberly-Clark Corporation) and 70 percent, by weight, secondary fibers (BJ de-inked secondary fiber pulp available from the Ponderosa Pulp Products—a division of Ponderosa Fibers of America, Atlanta, Ga.) and transferring the web onto a 0.4 osy (14 gsm) web of polypropylene spunbond filaments. Quaker 2008 de-bonding agent (Quaker Chemical Company) was added to the pulp fibers at levels of 0, 1, 2 and 3 percent based on the weight of the dry pulp fibers. The spunbond filaments were bonded utilizing a pattern having approximately 306 pin bonds per square inch and a total bond area of about 16 percent when contacted with a smooth anvil roll. The laminate, having a total basis weight of about 90 gsm, was hydraulically entangled into a composite material utilizing 4 manifolds. Each manifold was equipped with a jet strip having one row of 0.007 inch holes at a density of 30 holes per inch. Water pressure in the manifold was 600 psi (gage). The layers were supported on a 100 mesh stainless steel forming wire which travelled under the manifolds at a rate of about 20 fpm. The composite fabric was dried utilizing conventional through-air drying equipment. The nonwoven composite fabrics were tested to determine the static and dynamic coefficients of friction and as well as abrasion resistance on the low pulp fiber concentration side of the fabric. The results of the tests are reported in Table 8.

TABLE 8

SB ABRASION/COF DATA VS. DEBONDER LEVEL

| Sample | % Debonder | Martindale Abrasion Resistance | Static COF | DYN COF |
|---|---|---|---|---|
| 1 | 0 | 1.75 | .4317 | .3743 |
| 2 | 1 | 3.75 | .2835 | .2469 |
| 3 | 2 | 3.50 | .2937 | .2563 |
| 4 | 3 | 4.25 | .3189 | .2841 |

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method of making a high pulp content nonwoven composite fabric having from about 10 to about 25 percent, by weight, of a nonwoven continuous filament substrate; and more than about 70 percent, by weight, of a fibrous component consisting of pulp fibers, said method comprising:
    superposing a pulp fiber layer over a nonwoven continuous filament substrate having a bond density greater than about 100 pin bonds per square inch and a total bond area less than about 30 percent;
    hydraulically entangling said layers to form a composite material; and
    drying said composite.

2. The method of claim 1 wherein the layers are superposed by depositing pulp fibers onto the nonwoven continuous filament substrate by dry forming or wet-forming.

3. The method of claim 1 wherein the layers are superposed by combining a coherent sheet of pulp fibers with the nonwoven continuous filament substrate layer.

4. The method of claim 1 wherein the coherent sheet of pulp fibers is selected from the group consisting of a re-pulpable paper sheet, a re-pulpable tissue sheet, and a batt of wood pulp fibers.

5. The method of claim 1 wherein the pulp fiber layer is superposed over a continuous filament substrate having a bond density from about 250 to about 450 pin bonds per square inch and an overall bond area from about 5 percent to about 25 percent.

6. The method of claim 1 wherein the pulp fiber layer is superposed over a nonwoven web of continuous spunbonded filaments.

7. The method of claim 1 further comprising the step of adding a material selected from clays, activated charcoals, starches, particulates, and superabsorbent particulates to the superposed layers prior to hydraulic entangling.

8. The method of claim 1 further comprising the step of adding a material selected from clays, activated charcoals, starches, particulates, and superabsorbent particulates to the superposed, hydraulically entangled composite material.

9. The method of claim 2 further comprising the step of adding a material selected from clays, activated charcoals, starches, particulates, and superabsorbent particulates to a suspension of pulp fibers used to form the pulp fiber layer on the continuous filament substrate.

10. The method of claim 1 wherein the hydraulically entangled composite is subjected to a finishing step selected from mechanical softening, pressing, creping, and brushing.

11. The method of claim 1 wherein the hydraulically entangled composite is subjected to a chemical post-treatment selected from dyes and adhesives.

12. A method of making a high pulp content nonwoven composite fabric having from about 10 to about 25 percent, by weight, of a nonwoven continuous filament substrate; and more than about 70 percent, by weight, of a fibrous component consisting of pulp fibers, said method comprising:
  superposing a pulp fiber layer over a nonwoven continuous filament substrate;
  hydraulically entangling said layers to form a composite material; and
  drying said composite.

13. The method of claim 12 wherein the layers are superposed by depositing pulp fibers onto the nonwoven continuous filament substrate by dry forming or wet-forming.

14. The method of claim 12 wherein the layers are superposed by combining a coherent sheet of pulp fibers with the nonwoven continuous filament substrate layer.

15. The method of claim 12 wherein the coherent sheet of pulp fibers is selected from the group consisting of a re-pulpable paper sheet, a re-pulpable tissue sheet, and a bart of wood pulp fibers.

16. The method of claim 12 wherein the pulp fiber layer is superposed over a continuous filament substrate having a bond density greater than about 100 pin bonds per square inch and a total bond area less than about 30 percent.

17. The method of claim 12 wherein the pulp fiber layer is superposed over a nonwoven web of continuous spunbonded filaments.

18. The method of claim 12, further comprising the step of adding a material selected from clays, activated charcoals, starches, particulates, and superabsorbent particulates to the superposed layers prior to hydraulic entangling.

19. The method of claim 12 further comprising the step of adding a material selected from clays, activated charcoals, starches, particulates, and superabsorbent particulates to the hydraulically entangled composite material.

20. The method of claim 13 further comprising the step of adding a material selected from clays, activated charcoals, starches, particulates, and superabsorbent particulates to a suspension of pulp fibers used to form the pulp fiber layer on the continuous filament substrate.

21. The method of claim 12 wherein the hydraulically entangled composite is subjected to a finishing step selected from mechanical softening, pressing, creping, and brushing.

22. The method of claim 12 wherein the hydraulically entangled composite is subjected to a chemical post-treatment selected from dyes and adhesives.

23. A method of improving the abrasion resistance of a high pulp content nonwoven composite fabric having from about 10 to about 25 percent, by weight, of a nonwoven continuous filament substrate; and more than about 70 percent, by weight, of a fibrous component consisting of pulp fibers, said method comprising adding up to about 3 percent of a de-bonding agent to the high pulp content nonwoven composite fabric.

* * * * *